US00PP29273P2

(12) United States Plant Patent
Fryer

(10) Patent No.: US PP29,273 P2
(45) Date of Patent: May 8, 2018

(54) HYBRID TEA ROSE PLANT NAMED 'FRYRAPTURE'

(50) Latin Name: *Rosa hybrida*
Varietal Denomination: FRYrapture

(71) Applicant: Early Morning LLC, Lawrenceburg, IN (US)

(72) Inventor: Gareth Fryer, Knutsford (GB)

(73) Assignee: Early Morning LLC, Lawrenceburg, IN (US)

( * ) Notice: Subject to any disclaimer, the term of this patent is extended or adjusted under 35 U.S.C. 154(b) by 0 days. days.

(21) Appl. No.: 15/530,080

(22) Filed: Dec. 1, 2016

(51) Int. Cl.
*A01H 5/02* (2006.01)

(52) U.S. Cl.
USPC ..... Plt./138

(58) Field of Classification Search
USPC ..... Plt./138, 137
CPC ..... A01H 5/0222
See application file for complete search history.

(56) References Cited

U.S. PATENT DOCUMENTS

| | | | |
|---|---|---|---|
| PP6,262 | P | 8/1988 | Stephens et al. |
| PP9,274 | P | 9/1995 | Olesen et al. |
| PP23,476 | P2 | 3/2013 | Carruth |

OTHER PUBLICATIONS https://www.plantsmap.com/plants/32548/all-my-loving-hybrid-tea-rose; Apr. 27, 2016; 3 pages.*
Weeks Roses, 2017 Catalog, 92 pages.

* cited by examiner

*Primary Examiner* — Kent L Bell
(74) *Attorney, Agent, or Firm* — McKee, Voorhees & Sease, PLC

(57) ABSTRACT

A new variety of Hybrid Tea rose suitable for garden decoration, having flowers of dark even pink coloration.

1 Drawing Sheet

Classification: The present invention relates to a new *Rosa hybrida* plant.

Variety denomination: The new plant has the varietal denomination 'FRYrapture'.

BACKGROUND OF THE INVENTION

This invention relates to a new and distinct variety of Hybrid Tea Rose. It has as its seed parent the variety known as 'POUlari' (U.S. Plant Pat. No. 9,274) and as its pollen parent the variety known as 'STEbigpu' (U.S. Plant Pat. No. 6,262).

SUMMARY OF THE INVENTION

Among the features which distinguish the new variety from other presently available and commercial rose cultivars known to the inventor are the following combinations of characteristics: its elegant dark even pink high centered flowers, its excellent color stability throughout the life of the flowers and its abundant blooms on long cutting stems. The plant has a bushy upright growth habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'FRYrapture' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'POUlari' by the following combination of characteristics: whereas 'FRYrapture' bears very double flowers (about 30 to 50 petals) of dark even pink coloration, 'POUlari' bears flowers of white coloration with significantly heavier petalage (about 55 to 75 petals). The new variety has a bushy upright tall growth habit (about 190 to about 240 cm. in height), whereas the seed parent has an upright significantly shorter growth habit (about 60 to about 100 cm. in height).

The new variety may be distinguished from its pollen parent, 'STEbigpu' by the following combination of characteristics: whereas 'FRYrapture' bears very double flowers (about 30 to 50 petals) of dark even pink coloration, 'STEbigpu' bears flowers of reddish purple coloration with significantly heavier petalage (about 60 to 70 petals). The new variety has a moderate tea with slight spices fragrance, whereas the pollen parent has a rich rose fragrance.

COMPARISON WITH THE CLOSEST COMMERCIALLY AVAILABLE CULTIVAR

The new variety may be distinguished from its closest commercially available cultivar, 'WEKmerewby' (U.S. Plant Pat. No. 23,476) by the following combination of characteristics: whereas 'FRYrapture' bears very double flowers (about 30 to 50 petals) of dark even pink coloration, 'WEKmerewby' bears double flowers of saturate pink coloration with significantly lesser petalage (about 26 to 38 petals). The new variety has a moderate tea with slight spices fragrance, whereas the closest commercially available cultivar has a very strong damask to somewhat fruity fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers singly. Flowers are borne on strong medium to long length stems (about 40 to about 60 cm.). Outdoors, the plant blooms abundantly and nearly continuously during the growing season. The flowers have a moderate tea with slight spices fragrance.

BUD

The peduncle is about 8.0 to about 10.0 cm. in length, of average caliper (about 4.0 to 4.5 mm. in diameter), and stiff. It is almost completely smooth having only very few stipitate glands. Peduncle color is between 146B and 146C.

Before the calyx breaks, the, bud is about 3.5 to about 4.5 cm. in diameter at the widest point, about 4.0 to about 4.5 cm. in length, and pointed to ovoid in shape. The surface of the bud bears between 5 to 12 foliaceous appendages, some stipitate glands, usually with slender foliaceous parts extending beyond the tip of the bud about ⅓ or more of its length. Bud color is between 146B and 146C.

The sepals are 5 per flower, about 25 to about 45 mm. long and about 10 to about 11 mm. in width at the widest point. The outer surface color of the sepal is between 146B and 146C. The outer surface of the sepal is moderately rough and bears between 0 to 8 foliaceous appendages with some stipitate glands and hairs. The inner surface color of the sepal is near 138B. The inner surface of the sepal is covered with fine wooly tomentum; sepal margins are entire and lined with many stipitate glands and numerous hairs. The sepals are moderately fugacious and usually straight in shape with acute apices.

The receptacle of the flower is medium in size (about 8 mm. in length and about 4 mm. in diameter). The receptacle is funnel shaped in form. Its surface is smooth with an occasional stipitate gland and with moderately thick fleshy walls. The receptacle color is between 146B and 146C.

As the petals open (after the calyx breaks), the bud is about 4.0 to 4.5 cm. long and about 4.0 cm. in diameter at the widest point and pointed to ovoid in form. The color of the under surfaces of the newly opened petals is between 67A and 67B. At the point where the petal attaches, there is a small zone of between 2C and 2D. The color of the upper surfaces of the newly opened petals is between N66A and N66B. At the point where the petal attaches, there is a small zone of between 2C and 2D.

BLOOM

When fully open, the bloom ranges from about 10 to about 13 cm. in diameter with the largest flowers expressed under cool night temperature. Petalage is very double with about 30 to 50 petals and about 9 to 17 petaloids irregularly arranged. When partially open, the bloom form is high centered and petals are imbricated with petal edges somewhat reflexed outward. When fully open, the bloom form flattens somewhat leaving the flower as a shallow cup with petal edges somewhat reflexed outward.

PETALS

The substance of the petals is moderately heavy and of medium thickness, with upper surfaces somewhat satiny and under surfaces slightly shiny. The petals are about 4.5 to about 5.5 cm. in length and about 4.5 to about 5.0 cm. in width at the widest point. Petal margins are entire.

The outer petals are orbicular in shape with rounded apices and sometimes notched with one notch.

The inner petals are oval to obovate in shape with rounded apices and sometimes notched with one notch.

Petaloids are about 1.5 to about 3.5 cm. in length and about 1.5 to about 2.5 cm. in width at the widest point. Petaloids are irregularly shaped somewhat gladiate to oblanceolate with mucronate to acuminate apices.

NEWLY OPENED FLOWER

The under surface color of the outer, intermediate and inner petals is near 67A. At the point where the petal attaches, there is a small zone of between 2C and 2D. The upper surface color of the outer, intermediate and inner petals is between N66A and N66B. At the point where the petal attaches, there is a small zone of between 2C and 2D.

The under and upper surface colors of the petaloids are similar in coloration to the upper and under surfaces of the intermediate and inner petals.

The general tonality of the newly opened flower is between N66A and N66B.

THREE-DAY-OLD FLOWER

The upper surface color of the outer petal is near N66B. At the point where the petal attaches, there is a small zone of between 2C and 2D. The under surface color of the outer petals is between 67A and 67B. At the point where the petal attaches, there is a small zone of between 2C and 2D.

The under surface color of the intermediate and inner petals is near 67B. The upper surface color of the intermediate and inner petals is near N66B.

The under and upper surface colors of the petaloids are similar in coloration to the upper and under surfaces of the intermediate and inner petals.

The general tonality of the three-day-old flower is near N66B.

On the spent bloom, the petals usually drop off cleanly.

In October in Pomona, Calif., blooms on the bush growing outdoors generally last about five days. Cut roses from plants grown outdoors and kept at normal indoor living temperatures generally last about seven days.

MALE REPRODUCTIVE ORGANS

Stamens are many in number averaging about 45 to 60 and are arranged regularly about the pistils; a few are mixed with petaloids. The filaments are of medium length (about 3 to 4 mm.) most with anthers. Filaments are between 158C and 158D in color. The anthers are of medium size for the class and all open approximately at the same time. Anther color when immature is near 18C on the external part and near 19C on the internal part. Anther color at maturity is near 159A on the external part and near 159D on the internal part. Pollen is moderate to abundant and near 22C in color.

FEMALE REPRODUCTIVE ORGANS

Pistils vary in number (average about 80). The styles are moderately even, average in length (about 4 mm.), moderately heavy in caliper, and bunched. Stigma color is between 159A and 158D. Style color is near 184A. Ovaries are usually all enclosed in the calyx. The ovaries are small in size and near 2D in color.

Hips have not been observed on this variety when grown in Pomona, Calif.

FOLIAGE

The compound leaves are usually comprised of three to five to occasionally seven leaflets and are borne abundantly. The five-leaflet leaves are about 12 to about 13 cm. in length and about 10.0 cm. in width at the widest point, leathery in texture, and somewhat glossy in finish on the upper side and matte on the underside. The leaves have a reticulate venation pattern. The terminal leaflets are about 6.0 to about 6.5 cm. in length and about 4.0 cm. in width at the widest point, shaped ovate with mostly acute to subacute apices and rounded bases. Their margins are simply serrate.

The upper surface color of the mature leaf is between 146A and 146B. The under surface color of the mature leaf is between N138B and N138C. The under and upper colors of the leaf veins on the mature leaf are similar in coloration to the upper and under surfaces colors of the mature leaf. The upper surface color of the young leaf is between 178A and 178B. The under surface color of the young leaf is near 178B. The under and upper colors of the leaf veins on the young leaf are similar in coloration to the upper and under surfaces colors of the young leaf.

The rachis is about 6.0 to about 6.5 cm. in length and about 10 to about 20 mm. in width at the widest point and somewhat rough. The upper side is deeply grooved with some stipitate glands on the edges of the grooves. The underside of the rachis is somewhat rough with few stipitate glands and few small prickles. The rachis color is near 138B on the underside and near 146A on the upper side.

The stipules are about 10 to 13 mm. in length and about 8 mm. in width with somewhat short straight points that usually turn out at an angle of more than 45 degrees. The under and upper surface color of the stipule is between 138B and 146A. The upper and under surfaces of the stipules are smooth in texture.

The petiole is average in caliper and somewhat rough. The upper side is deeply grooved with some stipitate glands on the edges of the grooves. The underside of the petiole is somewhat rough with few stipitate glands and few small prickles. The petiole is about 7 to about 10 mm. in length and about 10 to about 20 mm. in width at the widest point. The petiole color is near 138B on the underside and near 146A on the upper side.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has a bushy upright tall growth habit (about 190 to about 240 cm. in height and about 150 to about 180 cm. in diameter at the widest point), with full branching. It displays vigorous growth and the canes are of medium caliper for the class (about 1.5 to about 2.0 cm. in diameter at the widest point).

The color of the major stems is between 137A and 137B. The major stems are rough in texture and they bear many large prickles that are about 6 to about 8 mm. in length. The large prickles are hooked slightly downward with a medium length oval base; prickle color is near 183A. The major stem bears many small prickles of similar shape and coloration.

The color of the branches is between 137A and 138B. The branches are rough in texture and they bear many large prickles which are of similar size and shape to the large prickles on the major stems; prickle color is near 183A. The branches have a few small prickles of similar shape and coloration.

The color of the new shoots is near 178B but quickly changes to near 137B. The new shoots are rough in texture and they bear many large prickles which are of similar size and shape to the large prickles on the major stems; prickle color is near 183A. The shoots bear a few small prickles of similar shape and coloration. New shoots when exposed to full sun are near 178A but quickly turn green.

I claim:

1. A new and distinct Hybrid Tea rose plant of the variety substantially as described and illustrated herein.

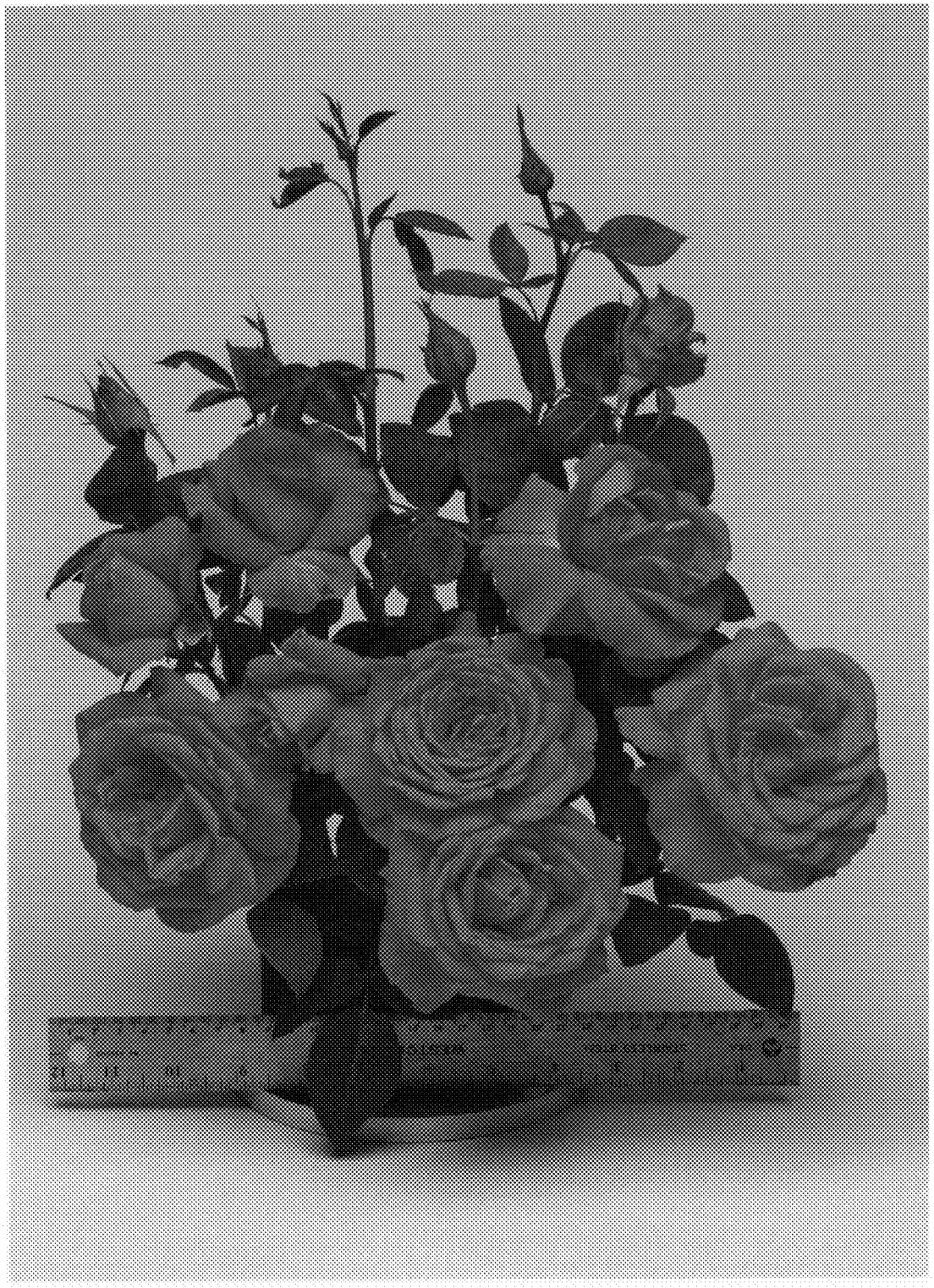

* * * * *